(12) United States Patent
Olbert et al.

(10) Patent No.: US 9,611,191 B2
(45) Date of Patent: Apr. 4, 2017

(54) REACTOR FOR CARRYING OUT AN AUTOTHERMAL GAS-PHASE DEHYDROGENATION

(71) Applicant: BASF SE, Ludwigshafen (DE)

(72) Inventors: Gerhard Olbert, Dossenheim (DE); Carlos Tellaeche Herranz, Heidelberg (DE); Norbert Asprion, Ludwigshafen (DE); Alexander Weck, Freinsheim (DE); Ellen Dahlhoff, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 364 days.

(21) Appl. No.: 14/103,322

(22) Filed: Dec. 11, 2013

(65) Prior Publication Data

US 2014/0171709 A1 Jun. 19, 2014

Related U.S. Application Data

(60) Provisional application No. 61/736,016, filed on Dec. 12, 2012.

(51) Int. Cl.
*C07C 5/48* (2006.01)
*B01J 8/04* (2006.01)
*B01J 19/24* (2006.01)

(52) U.S. Cl.
CPC ............... *C07C 5/48* (2013.01); *B01J 8/0453* (2013.01); *B01J 8/0492* (2013.01); *B01J 8/0496* (2013.01);
(Continued)

(58) Field of Classification Search
CPC .... B01J 8/0449; B01J 8/00453; B01J 8/0492; B01J 8/0496; B01J 19/2485; B01J 2208/00168; B01J 2208/00389; C07C 5/48
See application file for complete search history.

(56) References Cited

U.S. PATENT DOCUMENTS 3,475,136 A * 10/1969 Eschenbrenner ...... B01J 8/0005
422/148
7,034,195 B2 4/2006 Schindler et al.
(Continued)

FOREIGN PATENT DOCUMENTS

DE 40 26 566 A1 2/1992
EP 2506963 A1 10/2012
(Continued)

OTHER PUBLICATIONS

U.S. Appl. No. 14/103,322.
Translation of the International Preliminary Report on Patentabiltiy for PCT/EP2013/076154 dated Jun. 12, 2015.

*Primary Examiner* — Lessanework Seifu
(74) *Attorney, Agent, or Firm* — Drinker Biddle & Reath LLP; Geoffrey Zelley; Ashley Pezzner

(57) ABSTRACT

A reactor for gas-phase dehydrogenation of a hydrocarbon-comprising stream with an oxygen-comprising stream over a monolithic heterogeneous catalyst. Catalytically active zone(s) comprising monoliths packed next to one another and/or above one another and a mixing zone having fixed internals upstream of each catalytically active zone. Feed line(s) for the hydrocarbon-comprising gas stream to be dehydrogenated at the lower end of the reactor. Independently regulable feed line(s), which supply distributor(s), for the oxygen-comprising gas stream into each of the mixing zones and discharge line(s) for the reaction gas mixture of the autothermal gas-phase dehydrogenation at the upper end of the reactor. The interior wall of the reactor is provided with insulation. The catalytically active zone(s) is accessible from the outside of the reactor via manhole(s). The catalytically active zone(s), mixing zone, independently regulable feed line(s), and distributor(s), may be designed as one component which can individually be mounted and removed.

18 Claims, 12 Drawing Sheets

(52) U.S. Cl.
CPC .... *B01J 19/2485* (2013.01); *B01J 2208/0053* (2013.01); *B01J 2208/00168* (2013.01); *B01J 2208/00176* (2013.01); *B01J 2208/00221* (2013.01); *B01J 2219/2409* (2013.01); *B01J 2219/2411* (2013.01); *B01J 2219/2414* (2013.01); *B01J 2219/2419* (2013.01); *B01J 2219/2443* (2013.01)

(56) References Cited

U.S. PATENT DOCUMENTS

| | | |
|---|---|---|
| 2008/0119673 A1 | 5/2008 | Hechler et al. |
| 2010/0048960 A1* | 2/2010 | Degen ............... C07C 29/095 568/904 |
| 2011/0130607 A1 | 6/2011 | Kolios et al. |
| 2012/0157737 A1 | 6/2012 | Olbert et al. |
| 2013/0035529 A1 | 2/2013 | Olbert et al. |
| 2013/0035531 A1 | 2/2013 | Olbert et al. |

FOREIGN PATENT DOCUMENTS

| | | |
|---|---|---|
| WO | WO-2012084609 A1 | 6/2012 |
| WO | WO-2013/017608 A1 | 2/2013 |
| WO | WO-2013/017609 A1 | 2/2013 |

* cited by examiner

REACTOR FOR CARRYING OUT AN AUTOTHERMAL GAS-PHASE DEHYDROGENATION

CROSS-REFERENCE TO RELATED APPLICATIONS

This application claims the benefit of U.S. Provisional Application 61/736,016, filed Dec. 12, 2012, which is incorporated herein by reference.

The invention relates to a reactor for carrying out autothermal gas-phase dehydrogenations using a heterogeneous catalyst which is configured as a monolith and also to a process using the reactor.

Ceramic or metallic monoliths are established as catalyst supports for noble metal catalysts in mobile and stationary offgas purification. The channels offer a low flow resistance combined with a uniform accessibility to the outer catalyst surface for gaseous reaction media. This is advantageous compared to disordered beds in which a large pressure drop arises due to numerous deflections in the flow around the particles and the catalyst surface may not be utilized uniformly. The use of monoliths is of general interest for catalytic processes having high volume flows and adiabatic reaction conditions at high temperatures. In chemical process technology, these features apply in particular to dehydrogenation reactions which proceed in a temperature range from 400° C. to 700° C.

Progress in catalyst technology has made selective combustion of the dehydrogenation hydrogen in the presence of hydrocarbons possible, as described, for example, in U.S. Pat. No. 7,034,195. A suitable mode of operation is referred to as autothermal dehydrogenation and allows dehydrogenation reactors to be heated directly, so that complicated apparatus for indirect preheating and intermediate heating of the reaction mixture are dispensed with. Such a process is described, for example, in US 2008/0119673. However, this process has the serious disadvantage that the dehydrogenation is carried out over a heterogeneous catalyst in pellet form: the high flow resistance of beds of pellets requires a large reactor cross section and a correspondingly low flow velocity in order to limit the pressure drop in the catalytically active bed. This disadvantage is compensated by a very complicated apparatus for metered addition and distribution of the oxygen, which counters the advantage of the autothermal dehydrogenation.

EP-A 2 506 963 provides a reactor in the form of an essentially horizontal cylinder for carrying out an autothermal gas-phase dehydrogenation of a hydrocarbon-comprising gas stream by means of an oxygen-comprising gas stream to give a reaction mixture over a heterogeneous catalyst which is configured as a monolith, wherein
  the interior space of the reactor is divided by means of a detachable, cylindrical or prismatic housing G which is arranged in the longitudinal direction of the reactor and is gastight in the circumferential direction and open at the two end faces into
  an inner region A having one or more catalytically active zones, where in each case a packing made up of monoliths stacked on top of one another, next to one another and behind one another and in each case a mixing zone having fixed internals upstream of each catalytically active zone are provided, and
  an outer region B arranged coaxially to the inner region A,
  with one or more feed lines for the hydrocarbon-comprising gas stream to be dehydrogenated into the outer region B, deflection of the hydrocarbon stream to be dehydrogenated at one end of the reactor and introduction via a flow equalizer into the inner region A,
  with one or more, independently regulable, feed lines, where each feed line supplies one or more distribution chambers, for the oxygen-comprising gas stream into each of the mixing zones and
  with a discharge line for the reaction mixture of the autothermal gas-phase dehydrogenation at the same end of the reactor as the feed line for the hydrocarbon stream to be dehydrogenated.

A shell-and-tube heat exchanger having a bundle of tubes through which the reaction gas mixture for the autothermal gas-phase dehydrogenation is passed and having intermediate spaces between the tubes through which the hydrocarbon-comprising gas stream to be dehydrogenated is passed in countercurrent to the reaction mixture of the autothermal gas-phase dehydrogenation is advantageously provided at the reactor end at which the discharge line for the reaction gas mixture of the autothermal gas-phase dehydrogenation is arranged.

WO 2012/084609 proposes, proceeding from EP-A 2 506 963, a reactor which is improved from a safety point of view, according to which the outer region B is supplied with a gas which is inert under the reaction conditions of the autothermal gas-phase dehydrogenation and the hydrocarbon-comprising gas stream to be dehydrogenated is introduced via a feed line into the heat exchanger, by means of which the reaction gas mixture is heated in countercurrent by indirect heat exchange and is conveyed further to the end of the reactor opposite the heat exchanger, is deflected there, introduced via a flow equalizer into the inner region A and is mixed in the mixing zones with the oxygen-comprising gas stream, whereupon the autothermal gas-phase dehydrogenation takes place in the inner region A of the reactor.

However, the design of the above reactors is complicated, in particular as a result of the division of the interior of the reactor into an inner region and an outer region by provision of a housing arranged in the longitudinal direction of the reactor.

It was accordingly an object of the invention to provide a reactor for carrying out autothermal gas-phase dehydrogenations using a heterogeneous catalyst which is configured as a monolith, which reactor has a significantly simpler design than that mentioned above and ensures simple replacement of the monoliths, as required.

The object is achieved by a reactor in the form of a cylinder having a vertical longitudinal axis for carrying out an autothermal gas-phase dehydrogenation of a hydrocarbon-comprising gas stream by means of an oxygen-comprising gas stream to give a reaction gas mixture over a heterogeneous catalyst which is configured as a monolith, wherein
  one or more catalytically active zones each comprising a packing composed of monoliths stacked next to one another and/or above one another are arranged in the interior space of the reactor and a mixing zone having fixed internals is provided upstream of each catalytically active zone,
  with one or more feed lines for the hydrocarbon-comprising gas stream to be dehydrogenated at the lower end of the reactor,
  with one or more independently regulable feed lines, where each feed line supplies one or more distributors, for the oxygen-comprising gas stream into each of the mixing zones and with one or more discharge lines for the reaction gas mixture of the autothermal gas-phase dehydrogenation at the upper end of the reactor, where the interior wall of the reactor is provided over its entire area with an insulation layer, and where the one or each of the plurality of catalytically active zones is accessible from the outside of the reactor via in each case one or more manholes, or where the one or each of the plurality of catalytically active zones each comprising a packing composed of monoliths stacked next to one another and/or above one another including the mixing zone having fixed internals and being provided upstream of each catalytically active zone, the one or more independently regulable feed lines, and the one or more distributors, each supplied by one regulable feed line, is designed as one component which can individually be mounted and removed.

The individual components can, for example, be assembled and separated by means of welding seams.

In particular, the individual components can be assembled and separated by means of flanges.

In one embodiment, the object is achieved by a reactor in the form of a cylinder having a vertical longitudinal axis for carrying out an autothermal gas-phase dehydrogenation of a hydrocarbon-comprising gas stream by means of an oxygen-comprising gas stream to give a reaction gas mixture over a heterogeneous catalyst which is configured as a monolith, wherein one or more catalytically active zones each comprising a packing composed of monoliths stacked next to one another and/or above one another are arranged in the interior space of the reactor and a mixing zone having fixed internals is provided upstream of each catalytically active zone, with one or more feed lines for the hydrocarbon-comprising gas stream to be dehydrogenated at the lower end of the reactor, with one or more independently regulable feed lines, where each feed line supplies one or more distributors, for the oxygen-comprising gas stream into each of the mixing zones and with one or more discharge lines for the reaction gas mixture of the autothermal gas-phase dehydrogenation at the upper end of the reactor, where the one or each of the plurality of catalytically active zones is accessible from the outside of the reactor via in each case one or more manholes, and where the interior wall of the reactor is provided over its entire area with an insulation layer.

Thus, a reactor which is in the form of a cylinder having a vertical longitudinal axis, i.e. an upright apparatus, is proposed according to the invention.

The monoliths are installed in the catalytically active zones in such a way that flow through the channels of the monoliths occurs in the vertical direction.

The autothermal gas-phase dehydrogenation takes place over a heterogeneous catalyst which is present in the form of monoliths.

For the present purposes, a monolith is a one-piece, parallelepipedal block having a plurality of parallel channels which have a narrow cross section in the range from about 0.36 to 9 mm$^2$ and run right through the block. The channels preferably have a square cross section, in particular with a side length of the square in the range from 0.6 to 3 mm, particularly preferably from 1.0 to 1.5 mm.

The monoliths are preferably made of a ceramic material as support material on which a catalytically active layer has been applied, preferably by the washcoating process.

The most common material for monolithic structures is cordierite (a ceramic material composed of magnesium oxide, silicon oxide and aluminum oxide in a ratio of 2:5:2). Other materials whose monolith structures are commercially available are metals, mullite (mixed oxide of silicon oxide and aluminum oxide, ratio 2:3) and silicon carbide. These materials have, like cordierite, a low specific BET surface area (BET=Brunauer, Emmet and Teller) (e.g. in the case of cordierite typically 0.7 m$^2$/g).

Monolithic ceramic elements can be obtained with cell densities of 25-1600 cpsi (cells per square inch, corresponding to a cell size of 5-0.6 mm). The geometric surface area is increased by use of a higher cell density, so that the catalyst can be used more efficiently. Disadvantages of relatively high cell densities are somewhat more difficult production, more difficult coating with washcoat and a higher pressure drop over the reactor. Furthermore, the webs are generally thinner in the case of large cell densities, which reduces the mechanical stability of the monoliths. In cylindrical reactors, the monoliths have to be adapted in the peripheral region by means of appropriate cutting. However, the pressure drop remains very low for monoliths having a high cell density compared to a reactor packed with random packing elements (generally a factor of 10 lower), which can be attributed to the straight monolith channels.

To produce monolithic ceramic elements, it is possible to produce a mixture of talc, clay and an aluminum oxide-supplying component and silicon dioxide, mixing the mixture to form a molding composition, shaping the mixture, drying the raw product and heating it at a temperature of from 1200 to 1500° C., giving a ceramic which comprises mainly cordierite and has a low coefficient of thermal expansion. Generally speaking, a paste having appropriate rheological properties and an appropriate rheological composition can be extruded to form a monolith support. The paste generally comprises a mixture of ceramic powders of appropriate size, inorganic and/or organic additives, solvent (water), peptizing agent (acid) to set the pH and a permanent binder (colloidal solution or sol). The additives can be a plasticizer or a surfactant to set the viscosity of the paste or a temporary binder which can later be burnt out. Glass or carbon fibers are occasionally added to increase the mechanical strength of the monolith. The permanent binder is intended to improve the internal strength of the monolith.

Cordierite monoliths can be produced from a batch comprising talc, kaolin, calcined kaolin and aluminum oxide which together give a chemical compound of from 45 to 55% by weight of $SiO_2$, from 32 to 40% by weight of $Al_2O_3$ and from 12 to 15% by weight of MgO. Talc is a material which consists mainly of magnesium silicate hydrate, $Mg_3Si_4O_{10}(OH)_2$. The talc can, depending on source and purity, also be associated with other minerals such as tremolite ($CaMg_3(SiO_3)_4$), serpentine ($3MgO.2SiO_2, 2H_2O$), anthophyllite ($Mg_7(OH)_2(Si_4O_{11})_2$), magnesite ($MgCO_3$), mica and chlorite.

Monoliths can also be produced from other materials such as SiC, $B_4C$, $Si_3N_4$, BN, AlN, $Al_2O_3$, $ZrO_2$, mullite, Al titanate, $ZrB_2$, Sialon, perovskite, carbon and $TiO_2$ by extrusion.

Important factors in determining the properties of the monolith products produced by extrusion are the quality of the die, the type and properties of the materials used for producing the shapable mixture and also the additives added, the pH, the water content and the force used in extrusion. The additives employed in extrusion are, for example, celluloses, $CaCl_2$, ethylene glycols, diethylene glycols, alcohols, wax, paraffin, acids and heat-resistant inorganic fibers. Apart from water, it is also possible to use other solvents such as ketones, alcohols and ethers. The addition of additives can lead to improved properties of the monoliths, e.g. the formation of microcracks which improve the temperature change resistance, better porosity and better absorption capability and increased mechanical strength or low thermal expansion.

The bare monolithic structure is coated with a catalyst support layer comprising one or more ceramic oxides or a catalyst layer comprising the catalytically active metals and the optional further (promoter) elements previously applied to the ceramic oxide support material, with the coating being produced by a washcoat coating method.

Preferred variants for installation of the monoliths in the reactor are described in more detail below:

Variant 1:

The monoliths are stacked without a spacing next to one another and above one another, monolith against monolith, in the reactor, with flow through all monoliths in the vertical direction having to be ensured.

As a result of the method of manufacture, the monoliths have unevennesses and distortion, so that gaps of differing width are formed between directly adjacent monoliths during stacking. This leads to bypass of the reaction gas mixture. It is therefore necessary for the monoliths also to have a catalytic coating on their outer walls.

The monoliths have to be matched to the cylindrical inner wall of the reactor by cutting to the curvature of the reactor. The cutting to size is preferably carried out before delivery of the monoliths for installation in the reactor, since dust and scrap pieces obtained in this way can be passed directly to noble metal recycling.

The monoliths are installed in one or more layers, without a spacing, directly above one another or offset relative to one another. Preference is given to installing from 5 to 30 layers, in particular from 15 to 20 layers, above one another.

In a preferred variant, the individual layers are each rotated by 45° relative to one another, so that no continuous gaps in the packing are formed. The layers are preferably superposed in such a way that the corners of the monoliths of the next layer rest on the point at which four monoliths join in the layer underneath.

For installation of a horizontal layer, the procedure described below is preferably employed:

The cut-to-size peripheral pieces are firstly laid along the interior wall of the reactor and the individual monoliths are subsequently installed from the outside inward. The last four monoliths which fill the middle of the layer are inserted together and press the remaining monoliths of the layer firmly into the expandable mat seal introduced in the peripheral region next to the interior wall of the reactor.

In the above variant, the installation of temperature monitoring elements is difficult because these have, as a result of the method of manufacture, thicknesses which are greater than the channel widths of the monoliths and thus prevent flow through these. However, it is possible to install temperature monitoring elements in the gap between the monoliths, pull these outward into the expandable mat seal and from there lead them via ports to the outside of the reactor. Another installation variant for temperature monitoring elements is drilling through the monoliths and inserting a thermocouple sheath in which a multithermocouple is then installed.

Variant 1a:

In the following variant, it is possible to install thermocouples for temperature monitoring in a simple way without monolith channels having to be occupied by them. For this purpose, the monoliths are installed as described under variant 1 but a spacing is ensured between in each case directly superposed layers by introduction of thin sheet metal spacers which are installed, for example, in the form of a grating or as individual elements. This ensures spacings between in each case directly superposed monoliths in the range from 10 to 50 mm, preferably in the range from 10 to 20 mm.

Variant 2:

Variant 2 corresponds to variant 1a, i.e. a plurality of horizontal layers of monoliths which are installed above one another, spaced by means of spacers, are provided. Variant 2 differs from variant 1a in that the monoliths of each layer are in each case embedded on the sides through which the reaction gas mixture does not flow in expandable mats or mineral fiber nonwoven mats and thus sealed against one another.

Variant 3:

In variant 3, modules composed of two or more monoliths stacked next to one another and/or above one another are employed, with the monolith modules being dimensioned so that they can still be installed in the reactor via the manholes (access ports). The individual modules are enveloped around their periphery, leaving the openings for the reaction gas mixture passing through the monolith channels, in an expandable mat or in a mineral fiber nonwoven, in particular composed of a ceramic fiber, preferably polycrystalline mullite fibers, and inserted in a metallic casing having a clamping device. The individual modules are arranged next to one another and, with installation of sheet metal spacers as described under variant 1a, in layers above one another.

The reactor is operated at temperatures in the range from 500 to 690° C., preferably from 550 to 620° C., and flow through the reactor occurs from the bottom upward. During operation of the reactor, the metallic outer wall of the reactor expands to a greater extent than the ceramic monoliths, as a result of which the latter can become loose.

According to the invention, the interior wall of the reactor is therefore lined in the region of the monoliths with a pressure-stable insulation and the monoliths are sealed against this by means of expandable mats.

An advantage of the interior wall insulation is a reduction in the reactor wall temperature and thus lower thermal expansion of the reactor wall. Furthermore, an inexpensive material can be selected for the outer reactor wall because of the lower reactor wall temperature and the expandable mats have to provide less sealing effect in the peripheral region.

The monoliths according to variants 1 and 1a have to be coated over their entire surface, i.e. both in the channels and also on their outer surface.

The macroporous structure of ceramic monoliths aids the anchoring of the washcoat layer. The way of coating with the washcoat can be divided into two methods: the macroporous support can be (partially) filled with the washcoat material having a large surface area or a washcoat can be deposited as layer in the pores of the ceramic support. The filling of the pores leads to a very strong interaction between monolith and washcoat since the major part of the washcoat layer is actually fixed in the pores of the support and not only bound to the outer surface of the monolith channels. This type of coating is carried out using a solution (or a sol) of the material to be deposited or using a solution comprising very small colloidal particles. The disadvantage of coating by means of filling of the pores is that the amount of coating which can be deposited is limited since the pores become completely filled at some time and the washcoat becomes inaccessible.

Monoliths offer favorable preconditions for carrying out the autothermal dehydrogenation of hydrocarbons: in particular, narrower reactor cross sections and higher flow velocities compared to disordered packed fixed beds can be achieved, so that effective, gradated introduction of the oxygen into the main stream comprising hydrocarbon is possible. Owing to the smaller reactor cross section compared to disordered packed fixed beds, both the distributor and the fixed internals of the mixing zones are subjected to less mechanical stress, i.e. they sag to a lesser degree because of the shorter anchoring length. In addition, the main flow direction through the reactor is not limited to downward flow as in the case of disordered packed fixed beds.

After a prolonged period of operation, the catalysts recommended in the present text can normally be regenerated in a simple way, for example by firstly, in a first regeneration step, passing air which is (preferably) diluted with nitrogen and/or water vapor at an entry temperature of from 300 to 600° C. (in extreme cases also up to 750° C.), frequently from 500 to 600° C., through the fixed catalyst bed. The space velocity of regeneration gas over the catalyst (based on the total amount of regenerated catalyst) can be, for example, from 50 to 10 000 $h^{-1}$, and the oxygen content of the regeneration gas can be from 0.5 to 20% by volume.

After this, it is generally advisable to carry out further regeneration using pure molecular hydrogen or molecular hydrogen diluted with inert gas (preferably water vapor and/or nitrogen) (the hydrogen content should be ≥1% by volume) under otherwise identical conditions.

The monoliths stacked next to one another and above one another without a spacing to form a packing are preferably enveloped in an expandable mat or in a mineral fiber nonwoven and inserted in a casing having a clamping device. As mineral fiber nonwovens, preference is given to nonwovens as are known for use for offgas catalysts, for example Interam® mounting mats from 3M®.

Expandable mats are known from catalytic offgas purification and are described, for example, in DE-A 40 26 566: they consist essentially of ceramic fibers with embedded mica, in particular vermiculite. As a result of the embedded mica, the expandable mat attempts to expand with increasing temperatures, as a result of which the body enveloped therein is held particularly securely even at relatively high temperatures.

The mineral nonwovens or expandable mats are selected so that they expand under the action of heat and seal the generally ceramic monoliths from the housing, in particular prevent rubbing of the monoliths against the housing and also bypass flow of the reaction gas mixture at the interior wall of the housing.

The expandable mats in the peripheral region, in which the monoliths are enveloped, ensure a stable position of the latter since they generate a clamping force on thermal expansion. However, the clamping force can decrease during incorrect operation. A clamping device can therefore advantageously be provided.

Advantageously, the packings composed of monoliths stacked next to one another and/or above one another are built up of four or more than four partial packings; the partial packings are in each case individually equipped with a metal frame and can be assembled in such a way that they fill the entire cross-section of the reactor and can be sealed towards each other to avoid by-passes.

Alternatively or additionally, it is possible to assemble two or more than two partial packings on top of one another to give a packing.

Advantageously, all of the above described partial packings can be integrated in a casing in order to facilitate the handling.

In particular, the packings composed of monoliths stacked next to one another and/or above one another in each case rest on a support grating.

The support gratings are advantageously configured so that they do not block the channels for flow of the reaction gas mixture. To prevent this reliably, it is advantageous to provide, in the region directly adjoining the support grating, one or more layers of monoliths which have a significantly larger cross section of the channels compared to the other monoliths located further away from the support grating. The web thickness between the channels has to be sufficiently thin for the webs not to block the channels located above them.

As an alternative, one or more layers of a wire mesh can be provided on the support grating, with the mesh openings of the layer located directly on the support grating being somewhat larger and becoming increasingly small in the direction of the monoliths. Preference is given to mesh openings of from 5 to 15 mm and wire diameters of from 0.2 to 2 mm.

In addition or as an alternative, a layer of an open-pored foam ceramic, preferably one having a gap volume through which flow can occur from 70 to 90%, can be provided directly on the region adjoining the support grating.

A first layer of a high-porosity foam ceramic, in particular one having a free gap volume of about 70% and a height in the range from 10 to 100 mm, preferably in the range from 40 to 60 mm, can particularly preferably be provided in the region directly adjoining the support grating, superposed by a second layer formed by monoliths having a thickness of 50 mm and channels having a larger cross section compared to the other monoliths located further away from the support grating.

The interior wall of the reactor is continuously, i.e. over its entire length, and completely provided with an insulation layer.

In the region of the catalytically active zones, the insulation layer of the interior wall has to be pressure-resistant and very gastight. The insulation layer in the region of the catalytically active zones is preferably configured as a double layer having a first pressure-resistant layer resting against the interior wall of the reactor and a second layer which faces the interior of the reactor and is formed by an expandable mat.

Between the pressure-resistant layer provided on the interior wall of the reactor there is preferably a further layer which is significantly thinner in comparison and is formed by an expandable mat in order to ensure that the pressure-resistant layer is in very good contact with the interior wall of the reactor.

In the other regions of the interior wall of the reactor, i.e. in the region of the distributor and mixing zones, the insulation layer is preferably configured as a single layer composed of a high-temperature-stable fiber mat, in particular a polycrystalline mullite fiber, which has a sheet metal cladding on the side facing the interior of the reactor in order to prevent the reaction mixture from penetrating into the insulation layer.

The hydrocarbon-comprising gas stream to be dehydrogenated is introduced into the reactor at the lower end of the reactor and flows from the bottom upward through the reactor.

The hydrocarbon-comprising gas stream to be dehydrogenated is advantageously preheated, advantageously in a heat exchanger which is arranged above the uppermost catalytically active zone in the reactor or outside the reactor, with the hydrocarbon-comprising gas stream to be dehydrogenated being introduced via a feed line into the heat exchanger, being heated by the reaction gas mixture in countercurrent by indirect heat exchange in the heat exchanger and being conveyed further to the lower end of the reactor opposite the heat exchanger, deflected there, introduced via a port into the reactor and mixed in the mixing zones with the oxygen-comprising gas stream, whereupon the autothermal gas-phase dehydrogenation takes place in the catalytically active zones in the reactor.

The heat exchanger integrated into the reactor can, in particular, be configured as a shell-and-tube or plate heat exchanger operated in countercurrent.

The shell-and-tube heat exchanger is advantageously made of a highly heat-resistant stainless steel, in particular a stainless steel having the material number 1.4541 or 1.4910. The tubes of the shell-and-tube heat exchanger are installed at both ends of the tubes in tube plates, preferably without a gap, by backplate welding and the tube plates of the shell-and-tube heat exchanger are clad on the hot gas side of the tube plates with a heat-resistant stainless steel, in particular a stainless steel having the material number 1.4841. A heat exchanger having a floating head design is particularly advantageous.

The hydrocarbon-comprising gas stream to be dehydrogenated can advantageously be introduced at two or more points into the heat exchanger, preferably as a main stream having a relatively high mass flow and one or more secondary streams having a lower mass flow than the main stream.

For start-up of the reactor, it is advantageous to be able to bypass the heat exchanger:

The start-up of the reactor system, i.e. the heating of the system to the reaction temperature of the autothermal gas-phase dehydrogenation is described below.

The reactor system, i.e. the reactor, the heat exchanger and the connecting lines, is initially at ambient temperature and has to be brought to the operating temperature of the autothermal gas-phase dehydrogenation, in the case of the dehydrogenation of butane to about 550° C.

Step 1: Heating of the reactor to about 200° C.

The reactor system is heated by means of a heating gas which can, for example, be recycle gas or nitrogen and is introduced at about 230° C. via a feed line. During this procedure, the heat exchanger is short-circuited (bypassed) on the shell side, i.e. the heating gas flows directly into the reactor, heats the latter to about 200° C. and subsequently flows only through the tubes of the heat exchanger which it likewise heats and subsequently leaves the reactor system. The heating gas does not flow through the space within the shell surrounding the tubes of the heat exchanger.

Step 2: Flushing of the space within the shell so as to make this largely oxygen-free.

A temperature measuring device is provided at the tube-side exit from the heat exchanger. As soon as this indicates a temperature of about 200° C., bypassing on the heat exchanger is stopped and the heating gas is conveyed on the shell side in countercurrent through the heat exchanger. In this way, the space within the shell is flushed.

Step 3: Further heating of the reaction system by means of a fuel gas which is burnt in the reactor.

One or more fuel gas feed conduits with appropriate downstream mixing devices are provided in the feed line to the reactor. Suitable fuel gases are, in particular, hydrogen, natural gas or else the hydrocarbon to be dehydrogenated. Particular preference is given to hydrogen which ignites over the noble metal-comprising catalyst coating at about 200° C. and heats the reactor to the required operating temperature of, in particular, about 550° C. For this purpose, an oxygen-comprising stream, lean air or particularly preferably air can be fed in as feed gas. The distance from the injection of the fuel gas to the noble metal-comprising catalyst should be as short as possible. The concentration of the fuel gas used should, in particular, be limited so that the gas composition in the reactor system is outside the explosive range and in particular outside the detonation range under the prevailing operating conditions. The minimum fuel gas concentration is preferably likewise prescribed in such a way that the temperature increase achieved by combustion at the inlet of the reactor is sufficient to increase the temperature of the cold feed gas in the recuperative heat exchanger. When hydrogen is used as fuel gas, a concentration of about 1.4% by volume of hydrogen is particularly preferred.

In addition to the heat exchanger, one or more supplementary heating facilities for the hydrocarbon-comprising gas to be dehydrogenated are preferably provided.

An electric heating element which is, in particular, installed in a detachable manner, as a plug-in system or as muffle burner in the hydrocarbon-comprising gas stream to be dehydrogenated after exit of the latter from the heat exchanger is particularly preferably provided as supplementary heating facility.

The hydrocarbon-comprising gas stream flows from the bottom through a port into the reactor and is equalized by means of fixed internals before each catalytically active zone in each case in a mixing zone, so that the flow velocity of the gas stream downstream of the mixing zone has a deviation of not more than +/−2% from the average over the reactor cross section.

The oxygen-comprising gas stream is introduced into each of the mixing zones via one or more, independently regulable feed lines, with each feed line supplying one or more distributors.

The distributors can, in particular, be configured as ring distributors or parallel rod distributors.

Since the residence time after introduction of the oxygen-comprising gas into the hydrocarbon-comprising gas stream should be very short, in particular less than 60 ms, additional devices such as mixing plates, metal strips having an elongated or annular shape are advantageous in order to increase the intensity of mixing.

The feed lines for the oxygen-comprising gas stream are advantageously thermally compensated and fastened by means of holding brackets to the reactor wall.

Each mixing zone preferably comprises in each case a tube distributor formed by a plurality of parallel plug-in tubes which are arranged in a plane perpendicular to the longitudinal direction of the reactor and are connected to one or more distributor chambers and have a plurality of uniformly spaced exit openings for the oxygen-comprising gas stream from the plug-in tubes and also a plurality of uniformly spaced mixing elements.

The mixing elements are particularly preferably configured as mixing plates.

According to the invention, manholes, i.e. access ports, which are dimensioned so that a worker can get through them into the interior space of the reactor are provided so as to provide access to the one catalytically active zone or each of the plurality of catalytically active zones from outside the reactor. As a result, in conjunction with the upright arrangement of the reactor, each catalytically active zone can be accessed individually from outside the apparatus without parts of the apparatus having to be taken out for this purpose. Simple access via manholes makes it possible to remove or install each of the catalytically active packings and the corresponding support gratings individually.

The catalyst can be exchanged in a particularly easy, time-saving manner according to one embodiment of the reactor in the form of a cylinder having a vertical longitudinal axis for carrying out an autothermal gas-phase dehydrogenation of a hydrocarbon-comprising gas stream by means of an oxygen-comprising gas stream to give a reaction gas mixture over a heterogeneous catalyst which is configured as a monolith, wherein one or more catalytically active zones each comprising a packing composed of monoliths stacked next to one another and/or above one another are arranged in the interior space of the reactor and a mixing zone having fixed internals is provided upstream of each catalytically active zone, with one or more feed lines for the hydrocarbon-comprising gas stream to be dehydrogenated at the lower end of the reactor, with one or more independently regulable feed lines, where each feed line supplies one or more distributors, for the oxygen-comprising gas stream into each of the mixing zones and with one or more discharge lines for the reaction gas mixture of the autothermal gas-phase dehydrogenation at the upper end of the reactor, where the interior wall of the reactor is provided over its entire area with an insulation layer, and where the accessibility of the one or more catalytically active zones is not ensured by providing manholes, but where the one or each of the plurality of catalytically active zones each comprising a packing composed of monoliths stacked next to one another and/or above one another including the mixing zone having fixed internals and being provided upstream of each catalytically active zone and also including the one or more distributors, is designed as one component which can individually be mounted and removed.

According to this embodiment, each of the components can individually, largely as a whole be dismounted, for example by loosening the correspondent flanges, if necessary due to deactivation of the catalyst, whereupon only the connecting lines as well as the instrumentation and control devices have to be dismantled additionally. After the exchange of the monoliths forming or comprising the catalyst, the individual components can be re-mounted again in an accordingly simple manner.

The setting-up time according to this design can be reduced to $1/10$ in comparison to a similar reactor to be charged via manholes.

Moreover, omitting the manholes allows for a significant reduction of the catalyst-free clearance between successive monolith packings so that a reactor having the same capacity can be configured at a lower height. What is more, the residence time of the reaction mixture in the catalyst-free clearances is reduced due to its reduced volume which is particularly advantageous since uncontrollable secondary reactions can be avoided or significantly reduced.

The invention also provides a process for carrying out an autothermal gas-phase dehydrogenation using the above reactor.

Preference is given to using two or more reactors, with at least one reactor being utilized for the autothermal gas-phase dehydrogenation and at the same time at least one further reactor being regenerated.

The autothermal gas-phase dehydrogenation is preferably a dehydrogenation of propane, of butane, of isobutane, of butene to butadiene, of ethylbenzene to styrene or of ethane to ethylene.

The reactor of the invention can be produced in a technically simple manner; since the reactor wall is cylindrical, it is possible to use hemispherical plates, which are simple and inexpensive, at both ends of the reactor. In this way, the reactor can be made resistant to pressure pulses in an economical way.

Due to the outer reactor wall having a continuous layer of insulation on the inside, it is possible to make it of less demanding and thus cheaper materials.

The invention is illustrated below with the aid of a drawing.

BRIEF DESCRIPTION OF THE DRAWINGS

In the drawing, in detail.

In the figures, identical reference numerals in each case denote identical or corresponding features.

Figure 1:
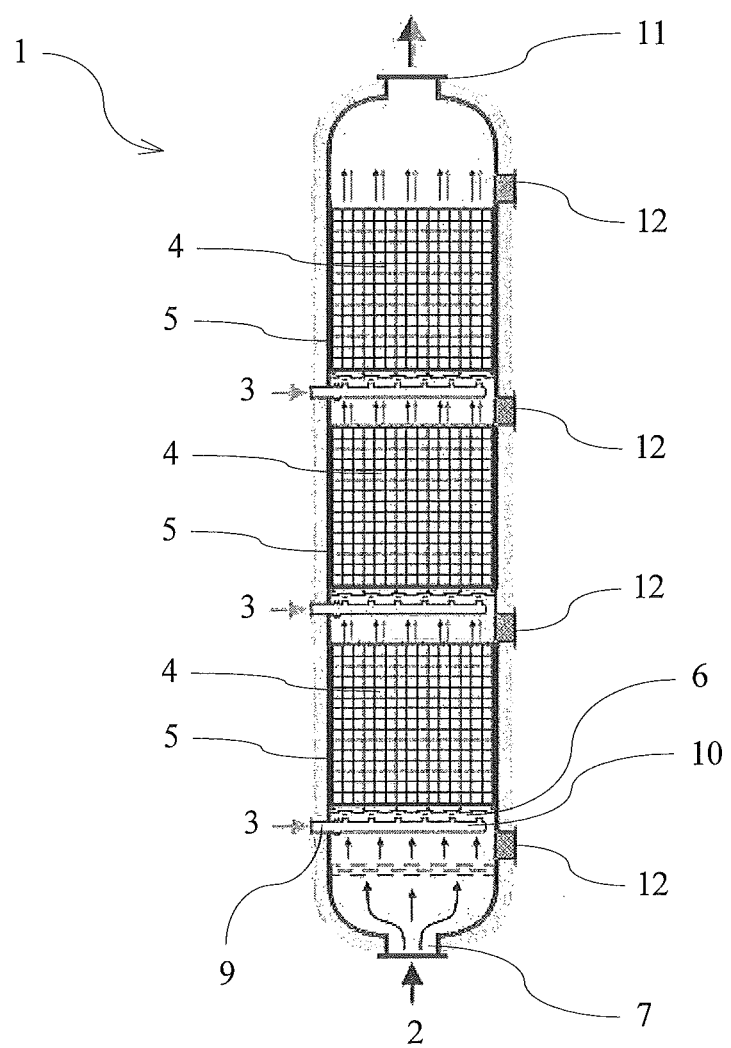
FIG. 1 schematically shows a preferred embodiment of a reactor according to the invention.

The schematic depiction in FIG. 1 shows a reactor 1 with introduction of a hydrocarbon-comprising gas stream 2 via a feed line 7 at the lower end of the reactor. Oxygen-comprising gas streams 3 are introduced via feed lines 9 into each of the mixing zones 6 which are in each case adjoined by a catalytically active zone 5 composed of monoliths 4 stacked next to one another and above one another. The reaction gas mixture leaves the reactor via the port 11 at the upper end of the reactor.

Figure 2:
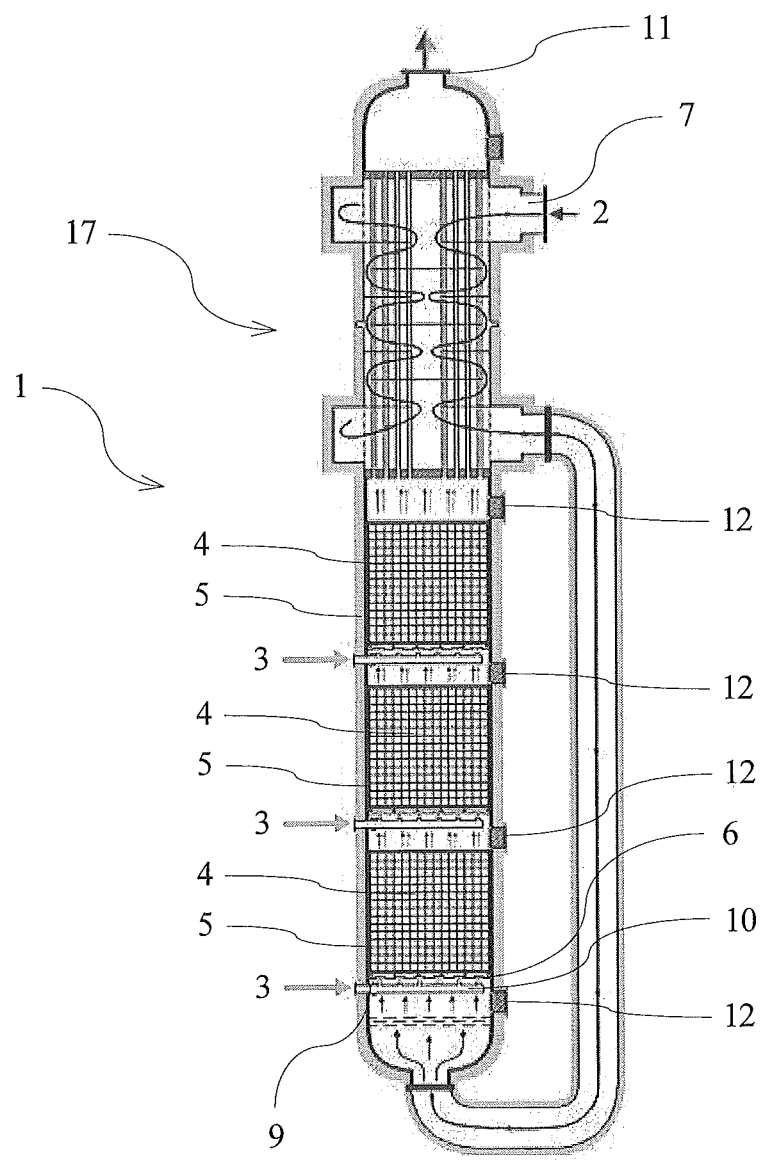
FIG. 2 shows a further preferred embodiment of a reactor according to the invention having an integrated heat exchanger, with a detail illustrated in FIG. 2A.

The embodiment shown in FIG. 2 differs from the embodiment in FIG. 1 in that a heat exchanger integrated into the reactor 1 at the upper end of the reactor is provided.

Figure 2A:
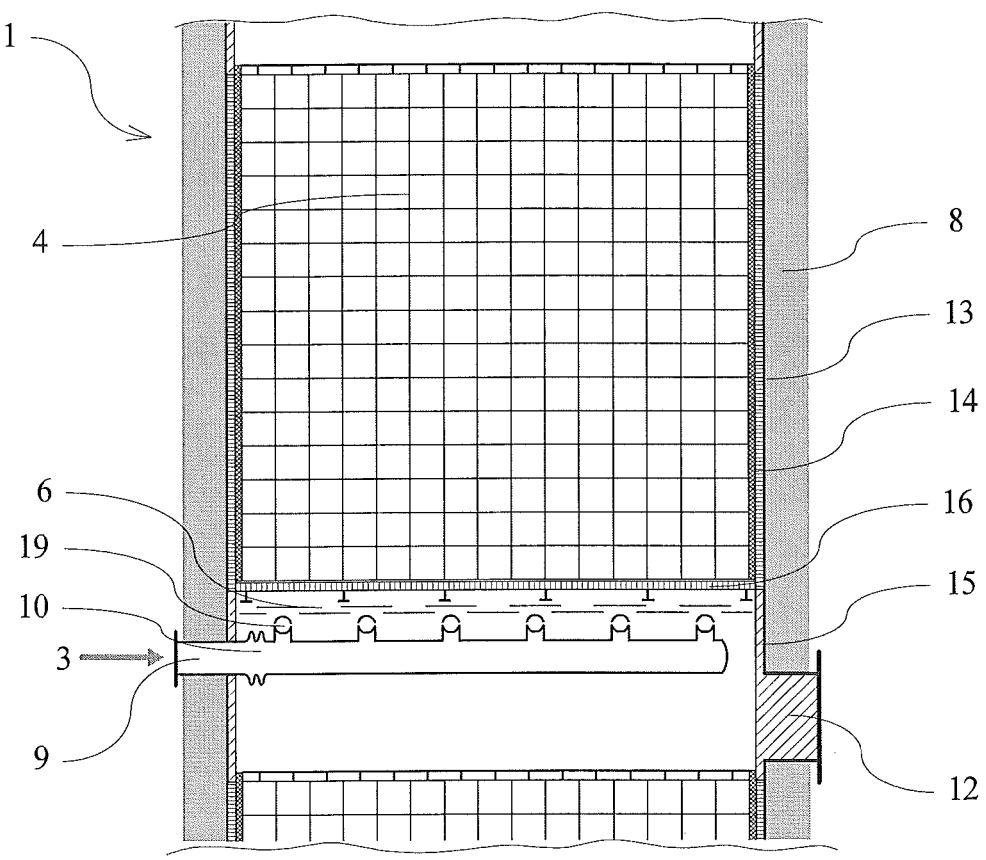

The detail shown in FIG. 2A illustrates the individual technical elements of a catalytically active zone 5 including the feed line 9 for the oxygen-comprising gas stream 3 and the manhole 12 ensuring the access of the monoliths of the packing in the catalytically active zone 5.

Figure 3:
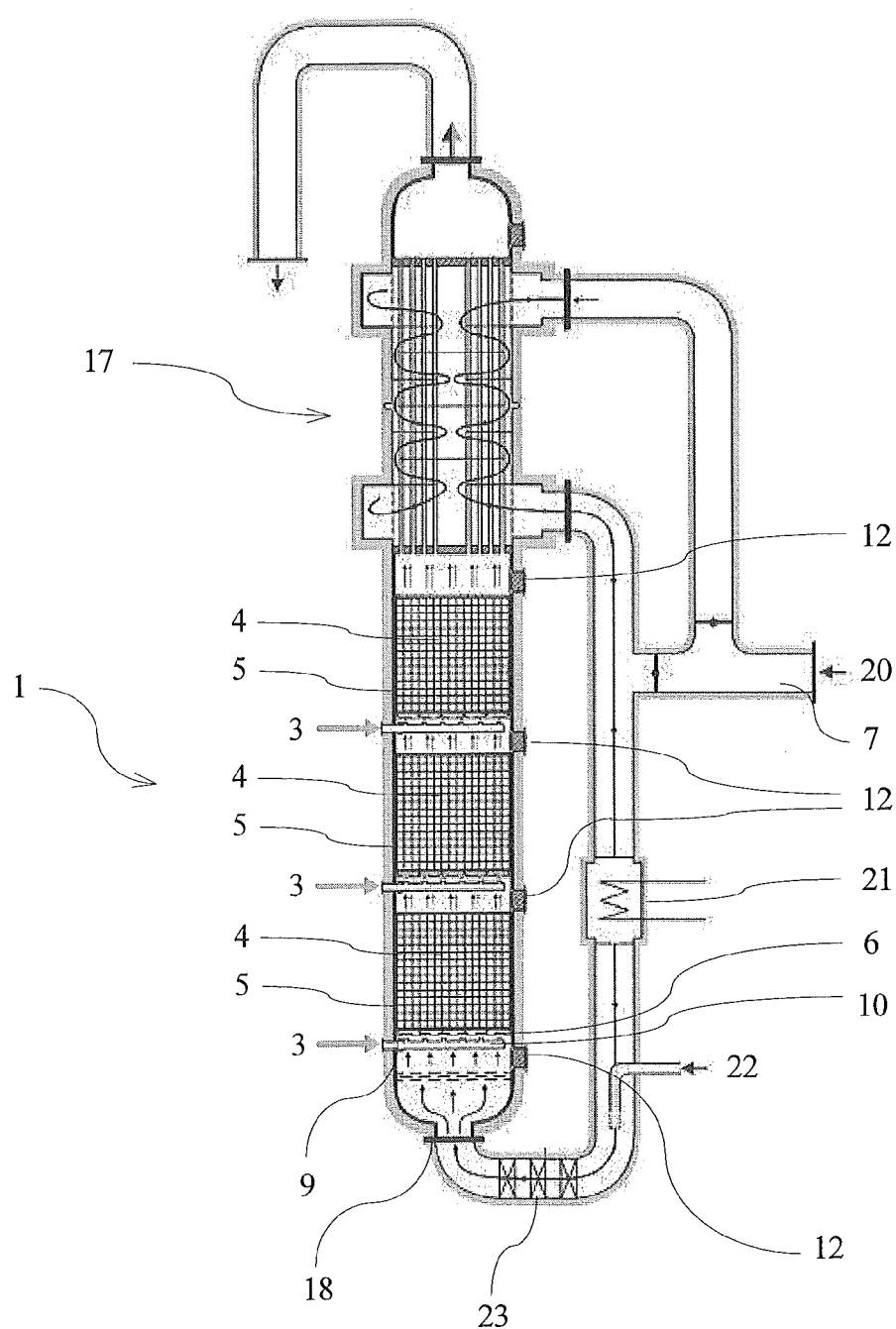
FIG. 3 shows a further preferred embodiment of a reactor according to the invention having a facility for heating-up with shell-side bypass of the heat exchanger.

The embodiment shown in FIG. 3 has additional facilities for heating the reactor system to the operating temperature, with shell-side bypass of the heat exchanger 17.

The heating gas 20 flows initially from the bottom upward through the reactor 1 and subsequently through the tubes of the heat exchanger 17. As soon as the gas stream exiting from the reactor at the upper end of the reactor has attained a temperature of about 200° C., the shell-side bypass of the heat exchanger 17 is stopped and the heating gas also flows through the space within the shell of the heat exchanger. An additional heat exchanger 21 is provided in the feed line for the heating gas to the reactor 1. For further heating of the reactor system, a fuel gas 22 is introduced via a mixer 23 into the reactor 1, at the lower end of the latter.

Figure 4:
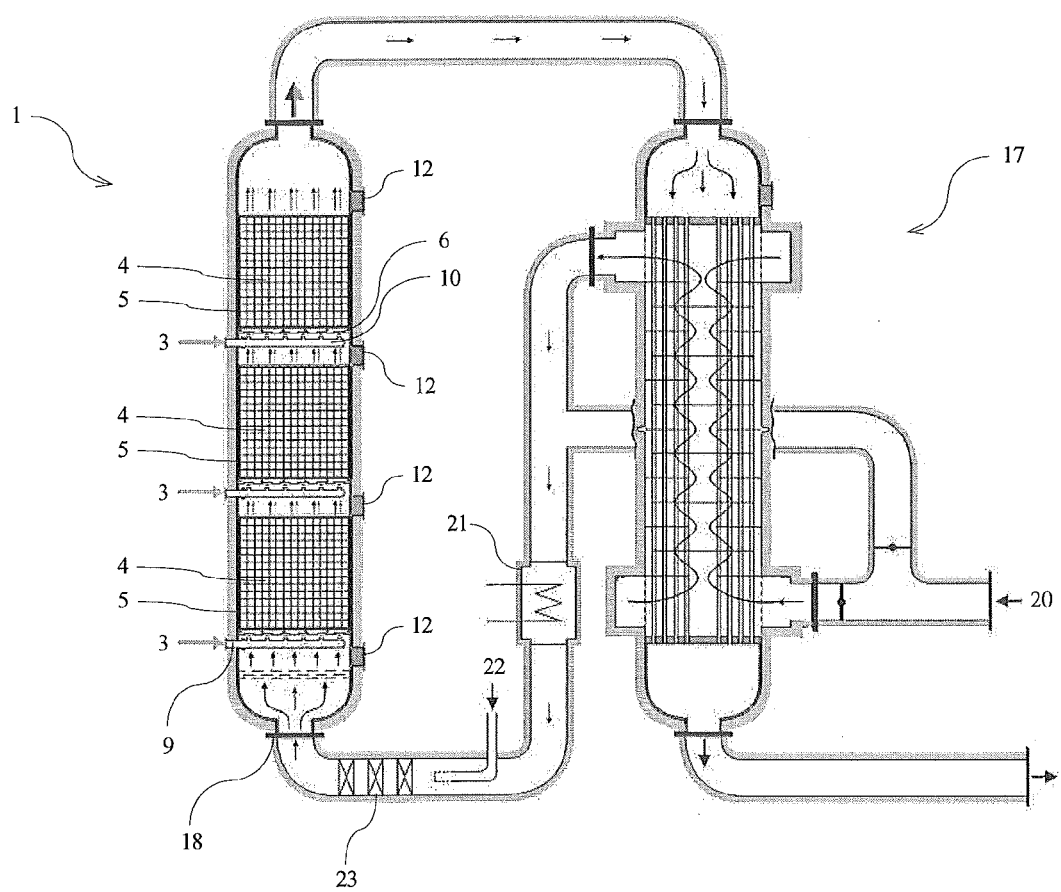
FIG. 4 shows a further preferred embodiment of a reactor according to the invention having a vertically arranged heat exchanger outside the reactor.

FIG. 4 shows a further preferred embodiment of a reactor 1 according to the invention having a vertically arranged heat exchanger 17 located at the side outside the reactor 1.

Figure 5:
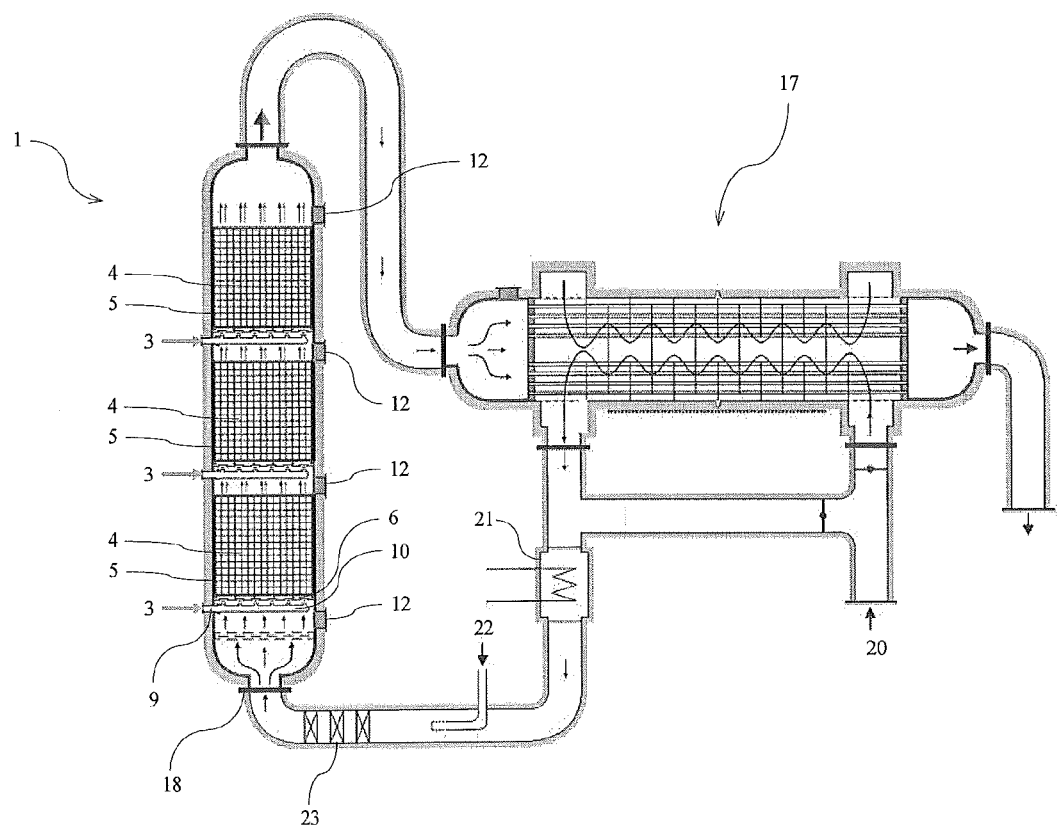
FIG. 5 shows a further preferred embodiment of a reactor according to the invention having a horizontally arranged heat exchanger outside the reactor.

FIG. 5 shows a further preferred embodiment of a reactor according to the invention having a horizontally arranged heat exchanger 17 located at the side outside the reactor 1.

Figure 6:
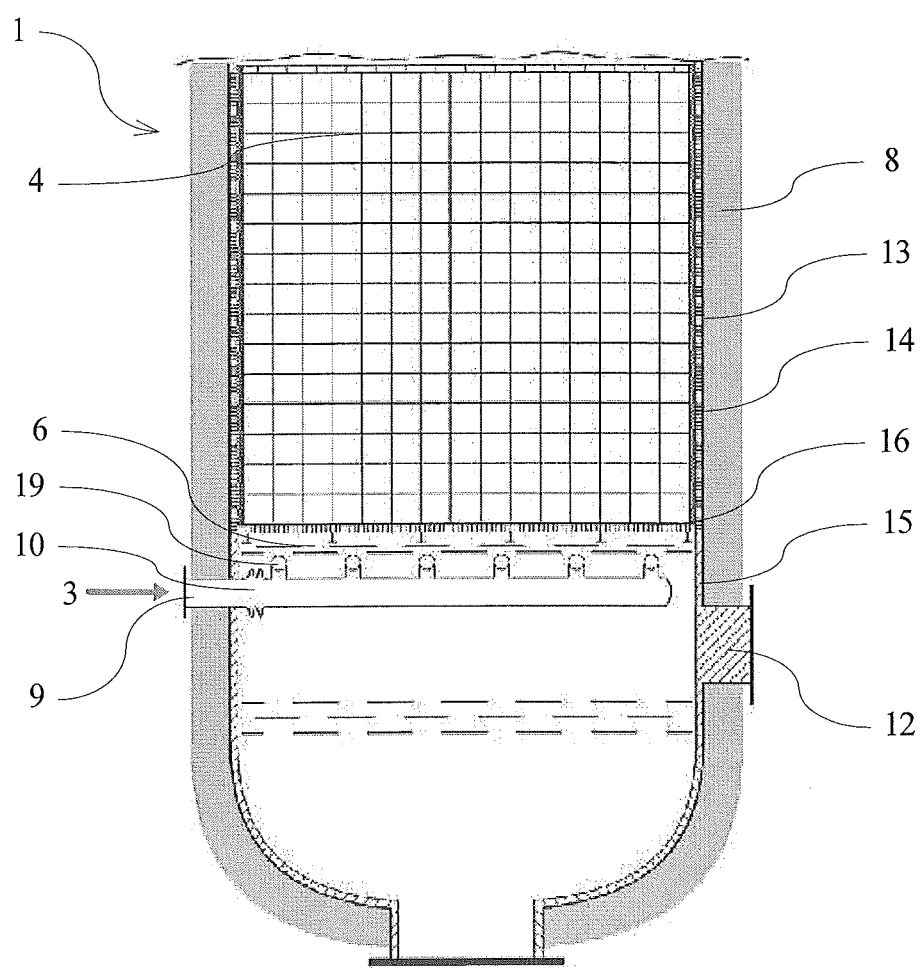
FIG. 6 shows a section of a preferred embodiment of a reactor according to the invention, FIG. 7 schematically shows an embodiment of a reactor according to the invention with individual components connected by means of flanges, the reaction mixture passing through the reactor from bottom to top, with details illustrated in FIGS. 7A and 7B, FIG. 8 schematically shows an embodiment of a reactor according to the invention analogously to FIG. 7, but the reaction mixture passing through the reactor from top to bottom, and FIG. 9 schematically shows an embodiment of a reactor according to the invention analogously to FIG. 7, with a heat exchanger arranged vertically outside the reactor.

The section shown in FIG. 6 illustrates the structure of the insulation layer which is provided on the interior wall of the reactor and in the region of the catalytically active zones 5 is a double layer having a first layer 13 which rests against the interior wall of the reactor and is made of a pressure-resistant material and also a second layer which faces the interior space of the reactor and is composed of an expandable mat.

In the other region, a single-layer insulation layer 15 which is made of a fiber mat and has sheet metal cladding on the side facing the interior space of the reactor is provided.

The section illustrates the introduction of the oxygen-comprising gas stream 3 via a distributor 10 formed by a plurality of plug-in tubes 19 arranged in the longitudinal direction of the reactor.

The figure also shows the support grating 16.

Figure 7:
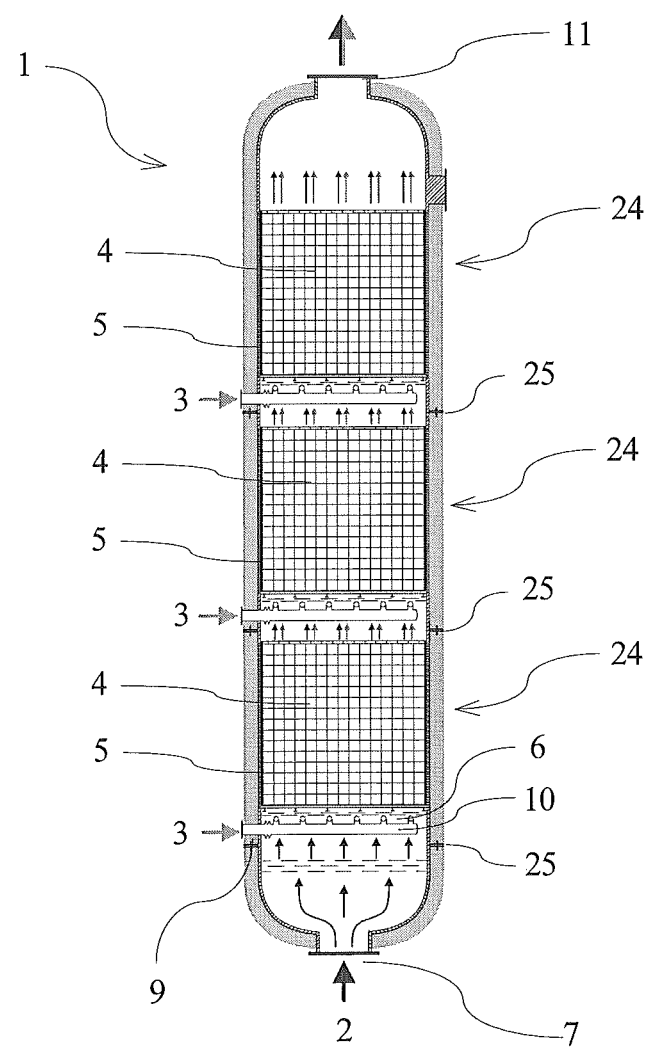
Figure 7A:
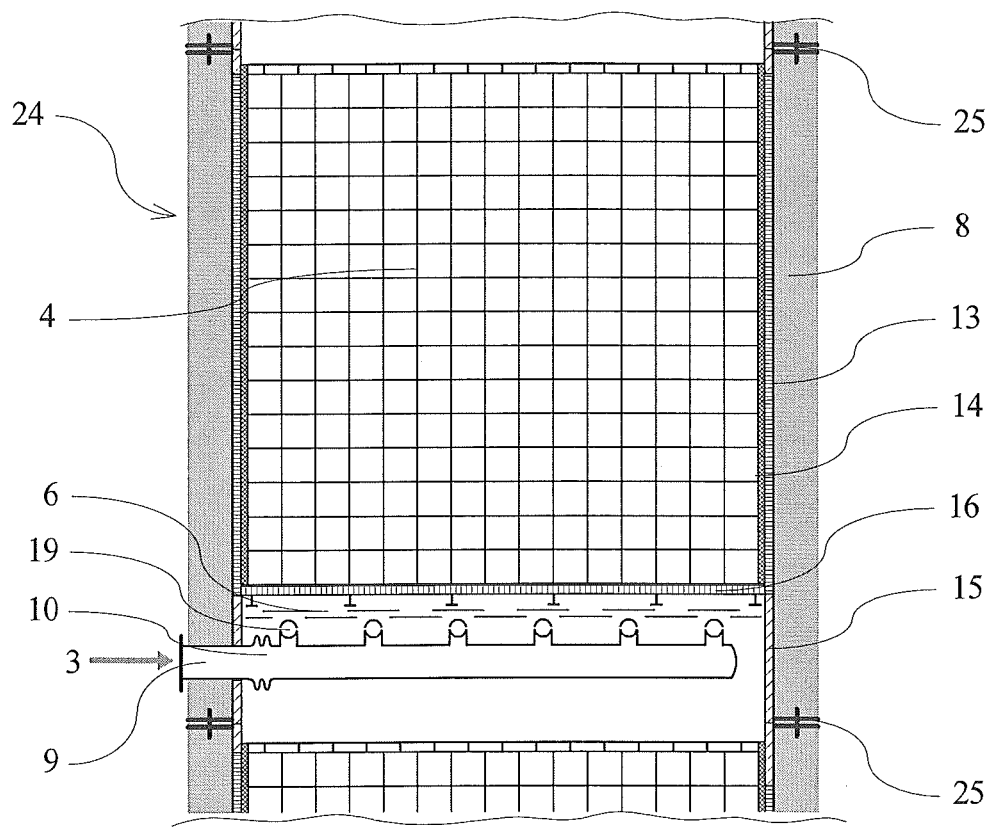
Figure 7B:
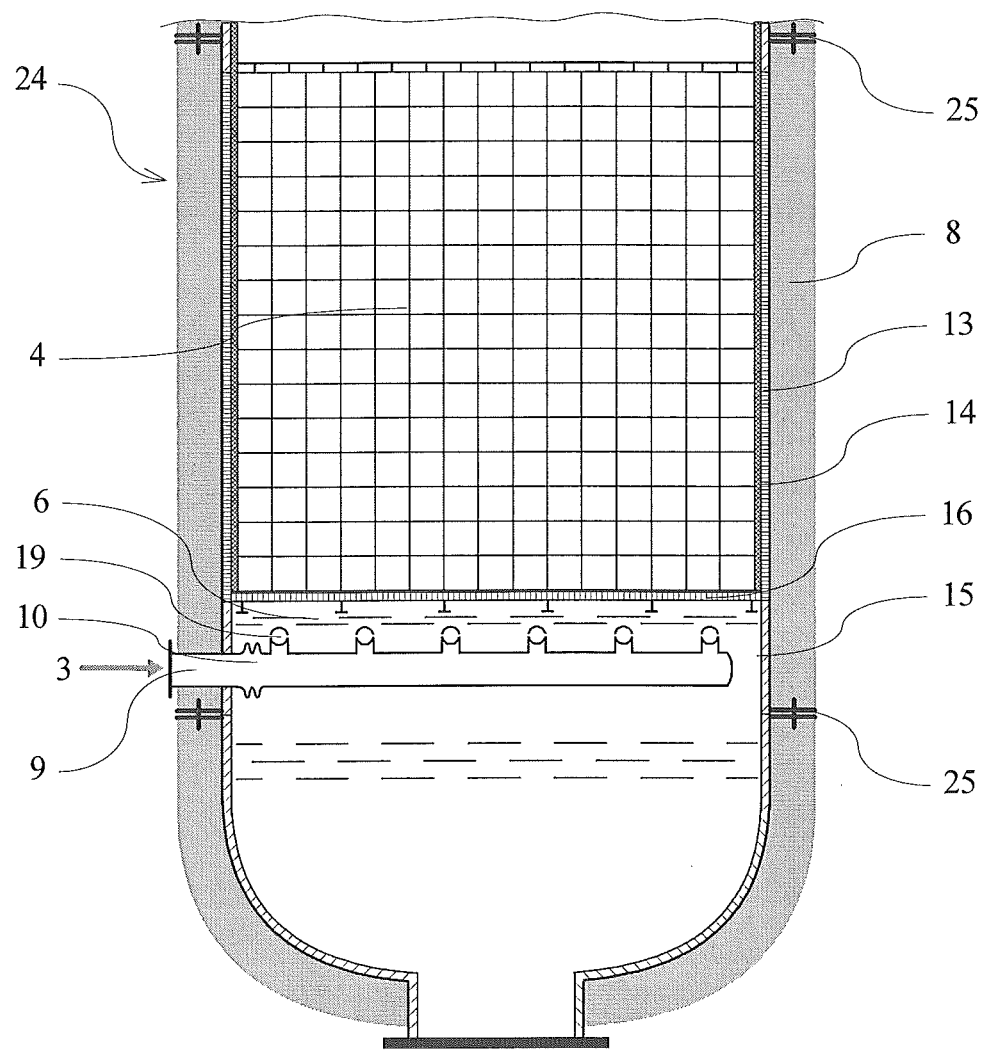

FIG. 7 shows an embodiment of a reactor according to the invention designed by way of example with three individual components 24 which can individually be mounted and removed, with a detailed illustration of a middle component 24 in FIG. 7A and of a bottom component 24 in FIG. 7B.

Figure 8:
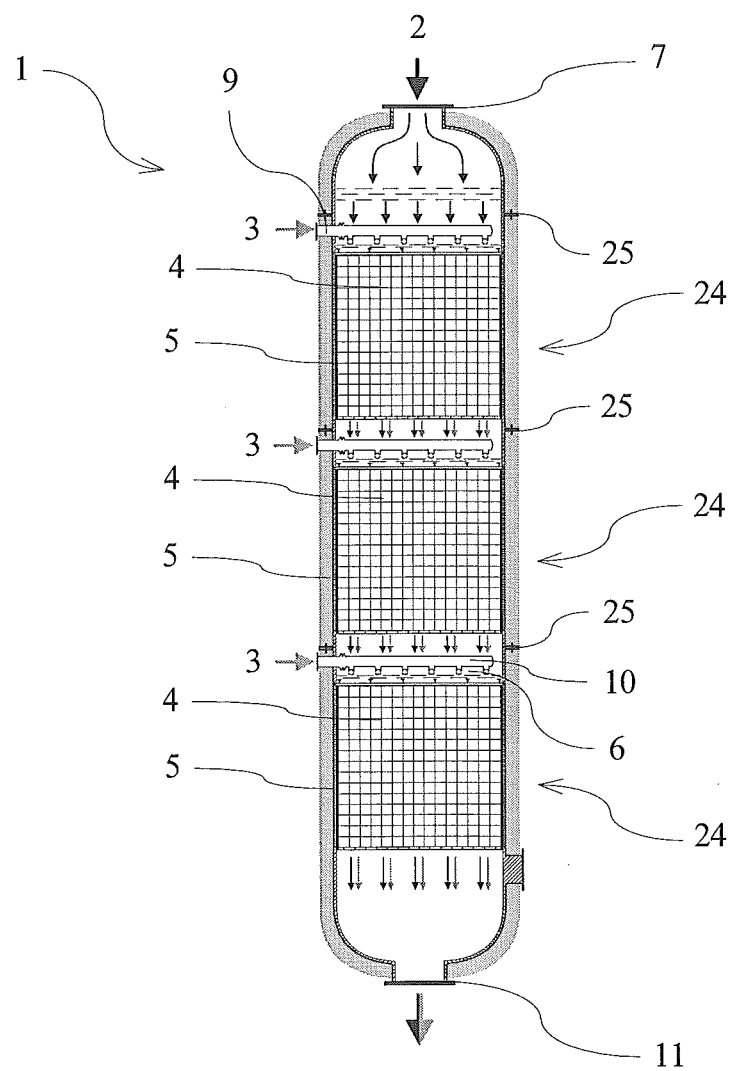

The reactor illustrated in FIG. 8 is the same as the reactor according to FIG. 7, but the flow direction of reaction mixture being reversed and the feed lines 9 for the oxygen-comprising gas stream being accordingly rearranged.

Both the reactors 1 illustrated in FIG. 7 and in FIG. 8 are assembled from components which can individually be mounted and removed.

Figure 9:
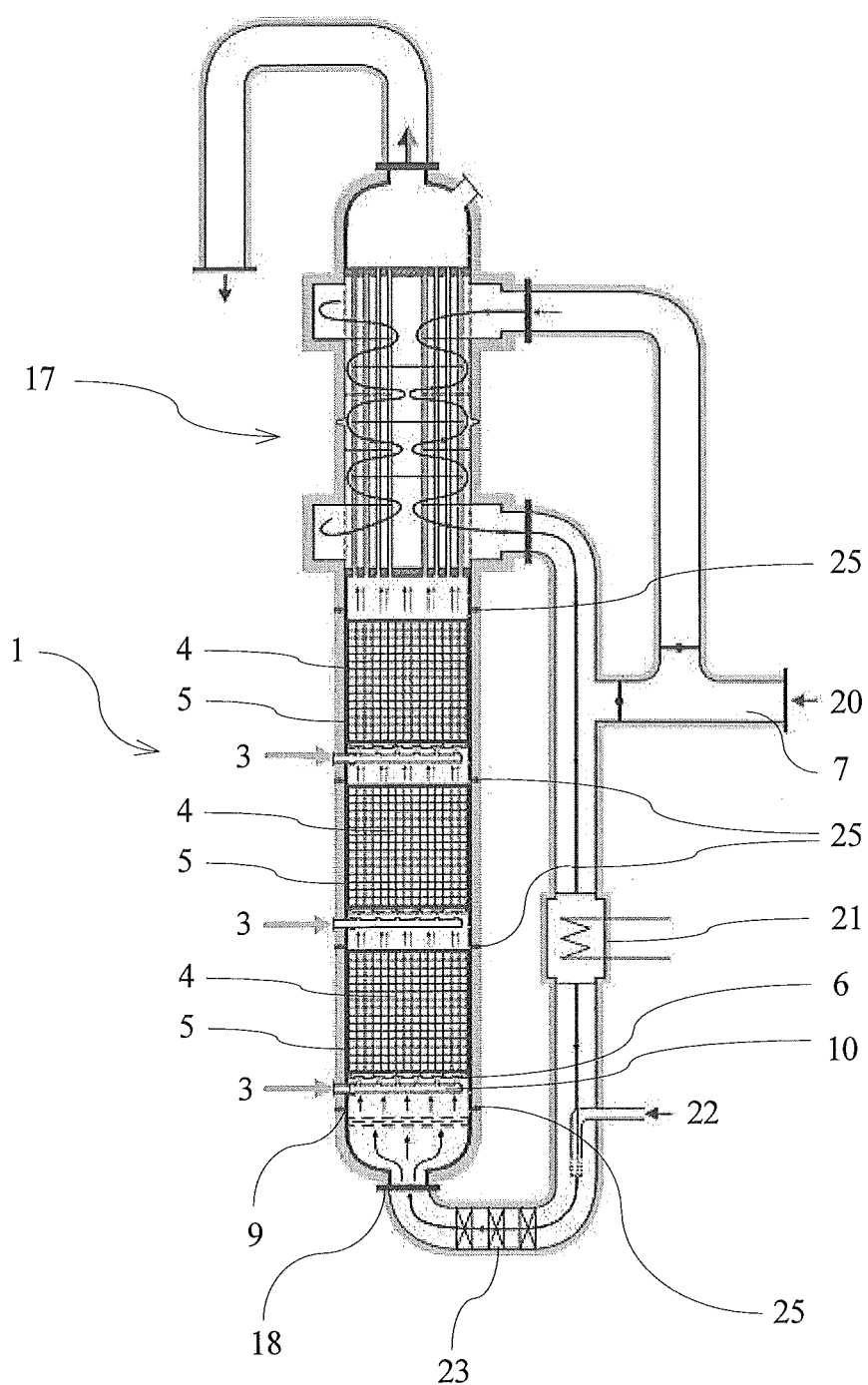

The reactor illustrated in FIG. 9 is the same as the reactor according to FIG. 3, but instead of having manholes to provide access to the monoliths, the individual components 24 are detachable connected to each other via flanges 25.

LIST OF REFERENCE NUMERALS

1 Reactor
2 Gas stream, comprising hydrocarbons
3 Gas stream, comprising oxygen
4 Monolith(s)
5 Catalytically active zone
6 Mixing zone
7 Feed line for gas stream 2
8 Exterior insulation
9 Feed line for gas stream 3
10 Distributor
11 Discharge line
12 Manhole
13 Dimensionally stable insulation
14 Seal
15 Protective insulation
16 Support grating
17 Heat exchanger
18 Port
19 Plug-in tubes
20 Heating gas
21 Additional heat exchanger
22 Fuel gas
23 Mixer
24 Component
25 Flange

The invention claimed is:

1. A reactor in the form of a cylinder having a vertical longitudinal axis for carrying out an autothermal gas-phase dehydrogenation of a hydrocarbon-comprising gas stream by means of an oxygen-comprising gas stream to give a reaction gas mixture over a heterogeneous catalyst which is configured as a monolith, wherein
   one or more catalytically active zones each comprising a packing composed of monoliths stacked next to one another and/or above one another are arranged in the interior space of the reactor and a mixing zone having fixed internals is provided upstream of each catalytically active zone,
   with one or more feed lines for the hydrocarbon-comprising gas stream to be dehydrogenated at the lower end of the reactor,
   with one or more independently regulable feed lines, where each independently regulable feed line supplies one or more distributors, for the oxygen-comprising gas stream into each of the mixing zones and
   with one or more discharge lines for the reaction gas mixture of the autothermal gas-phase dehydrogenation at the upper end of the reactor,
   where the interior wall of the reactor is provided over its entire area with an insulation layer, and
   where the one or each of the plurality of catalytically active zones each comprising a packing composed of monoliths stacked next to one another and/or above one another including
      the mixing zone having fixed internals and being provided upstream of each catalytically active zone,
      the one or more independently regulable feed lines, and
      the one or more distributors, each supplied by one independently regulable feed line, is designed as one component which can individually be mounted and removed.

2. The reactor according to claim 1, wherein the component can individually be mounted and removed by means of flanges.

3. The reactor according to claim 1, wherein the insulation layer is a double layer having a first pressure-stable layer resting against the interior wall of the reactor and a second layer formed by an expandable mat facing the interior of the reactor in the region of the catalytically active zones and is in the form of a single layer composed of a high-temperature-stable fiber mat provided on the side facing the interior of the reactor with a sheet metal cladding in the other regions.

4. The reactor according to claim 1, wherein the packing composed of monoliths stacked next to one another and above one another rests on a support grating, with the region directly adjoining the support grating being provided with one or more layers of monoliths which have channels having a larger cross section compared to the other monoliths located further away from the support grating.

5. The reactor according to claim 4, wherein the region directly adjoining the support grating is provided with a layer of an open-pored foam ceramic having a gap volume through which flow occurs of from 70 to 90%.

6. The reactor according to claim 4, wherein the region directly adjoining the support grating is provided with a first layer of a high-porosity open-pored foam ceramic and a second layer formed by monoliths which have channels having a larger cross section compared to the other monoliths located further away from the support grating is located above the first layer.

7. The reactor according to claim 1, wherein a heat exchanger is arranged above the uppermost catalytically active zone or outside the reactor, where the hydrocarbon-comprising gas stream to be dehydrogenated is introduced via a feed line into the heat exchanger, heated by the reaction gas mixture in countercurrent by indirect heat exchange in the heat exchanger and conveyed further to the lower end of the reactor, introduced via a port into the reactor and mixed with the oxygen-comprising gas stream in the mixing zones, whereupon the autothermal gas-phase dehydrogenation takes place in the reactor.

8. The reactor according to claim 7, wherein the heat exchanger can be mounted and removed by means of flanges.

9. The reactor according to claim 7, wherein the hydrocarbon-comprising gas stream to be dehydrogenated is introduced at two or more points into the heat exchanger, preferably as a main stream having a relatively high mass flow and one or more secondary streams having a lower mass flow than the main stream.

10. The reactor according to claim 7, wherein one or more supplementary heating facilities are provided in addition to the heat exchanger for the hydrocarbon-comprising gas stream to be dehydrogenated.

11. The reactor according to claim 10, wherein an electric heating element, which is preferably configured so as to be detachable, as a plug-in system or as a muffle burner, is provided as supplementary heating facility in the hydrocarbon-comprising gas stream to be dehydrogenated after the stream leaves the heat exchanger.

12. The reactor according to claim 1, wherein two or more catalytically active zones each having a packing composed of monoliths stacked next to one another and above one another are provided in the reactor.

13. The reactor according to claim 1, wherein the monoliths within the same catalytically active zone in each case have a different catalytic activity.

14. The reactor according to claim 12, wherein the two or more catalytically active zones in each case have a different catalytic activity.

15. The reactor according to claim 1, wherein the monoliths stacked next to one another and above one another to form a packing are enveloped in an expandable mat or in a mineral fiber nonwoven and inserted in a casing having a clamping device.

16. The reactor according to claim 1, wherein each mixing zone comprises in each case a tube distributor configured as a plurality of parallel plug-in tubes which are arranged in a plane perpendicular to the longitudinal direction of the reactor and are connected to one or more distribution chambers and have a plurality of uniformly spaced exit openings for the oxygen-comprising gas stream from the plug-in tubes, and also a plurality of uniformly spaced mixing elements.

17. The reactor according to claim 4, wherein the region directly adjoining the support grating is provided with a first layer of a high-porosity open-pored foam ceramic, with a height from 10 to 100 mm, and a second layer formed by monoliths which have channels having a larger cross section compared to the other monoliths located further away from the support grating is located above the first layer.

18. A process comprising carrying out an autothermal gas-phase dehydrogenation in the reactor according to claim 1, wherein the autothermal gas-phase dehydrogenation is a dehydrogenation of propane, of butane, of isobutane, of butene to butadiene, of ethylbenzene to styrene or of ethane to ethene.

* * * * *